(12) United States Patent
Manders

(10) Patent No.: US 8,007,532 B2
(45) Date of Patent: Aug. 30, 2011

(54) DIMENSIONALLY ADJUSTABLE SOFT TISSUE EXPANDER

(76) Inventor: Ernest K. Manders, Pittsburgh, PA (US)

(*) Notice: Subject to any disclaimer, the term of this patent is extended or adjusted under 35 U.S.C. 154(b) by 475 days.

(21) Appl. No.: 11/758,039

(22) Filed: Jun. 5, 2007

(65) Prior Publication Data

US 2008/0306505 A1    Dec. 11, 2008

(51) Int. Cl.
*A61F 2/12* (2006.01)
(52) U.S. Cl. .......................................................... 623/8
(58) Field of Classification Search ............... 623/1.12, 623/17.15, 17.16, 7–8
See application file for complete search history.

(56) References Cited

U.S. PATENT DOCUMENTS

| | | | |
|---|---|---|---|
| 4,217,889 A | 8/1980 | Radovan et al. | |
| 4,447,227 A | 5/1984 | Kotsanis | |
| 4,574,780 A | 3/1986 | Manders | |
| 4,950,292 A | 8/1990 | Audretsch | |
| 4,955,395 A | 9/1990 | Manders | |
| 5,026,394 A * | 6/1991 | Baker | 623/8 |
| 5,092,889 A * | 3/1992 | Campbell, Jr. | 623/23.47 |
| 5,441,540 A | 8/1995 | Kim | |
| 5,456,246 A * | 10/1995 | Schmieding et al. | 600/201 |
| 5,542,210 A * | 8/1996 | Hupfl | 47/47 |
| 5,571,179 A * | 11/1996 | Manders et al. | 623/8 |
| 5,618,310 A | 4/1997 | Ger et al. | |
| 5,649,978 A | 7/1997 | Samson | |
| 6,228,116 B1 | 5/2001 | Ledergerber | |
| 6,875,233 B1 | 4/2005 | Turner | |
| 2002/0111533 A1 * | 8/2002 | Melvin | 600/37 |
| 2002/0128716 A1 * | 9/2002 | Cohen et al. | 623/17.15 |
| 2004/0002726 A1 | 1/2004 | Nunez et al. | |
| 2004/0254625 A1 | 12/2004 | Stephens et al. | |
| 2006/0249943 A1 | 11/2006 | Bauer et al. | |
| 2008/0288068 A1 * | 11/2008 | Kronowitz | 623/8 |
| 2009/0082864 A1 * | 3/2009 | Chen et al. | 623/8 |
| 2010/0137999 A1 * | 6/2010 | Shohat | 623/23.75 |
| 2010/0217388 A1 * | 8/2010 | Cohen et al. | 623/8 |

FOREIGN PATENT DOCUMENTS

| | | |
|---|---|---|
| EP | 0338701 | 6/1992 |
| EP | 1702571 | 9/2006 |

OTHER PUBLICATIONS

McGhan Catalog Materials—2003.

* cited by examiner

*Primary Examiner* — Suzette J Gherbi
(74) *Attorney, Agent, or Firm* — Hooker & Habib, P.C.

(57) ABSTRACT

A soft tissue expander includes an expandable cover, a base, an adjustable central portion and a connecting member joined to side portions and extending across the central portion to determine the width of the expander.

31 Claims, 3 Drawing Sheets

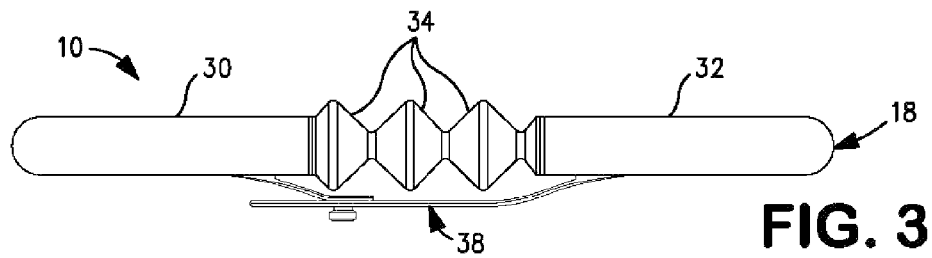
FIG. 3
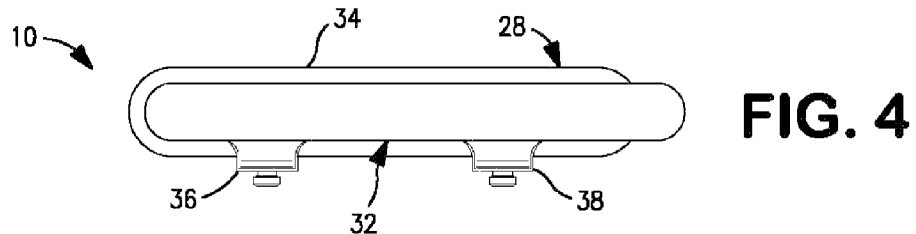
FIG. 4
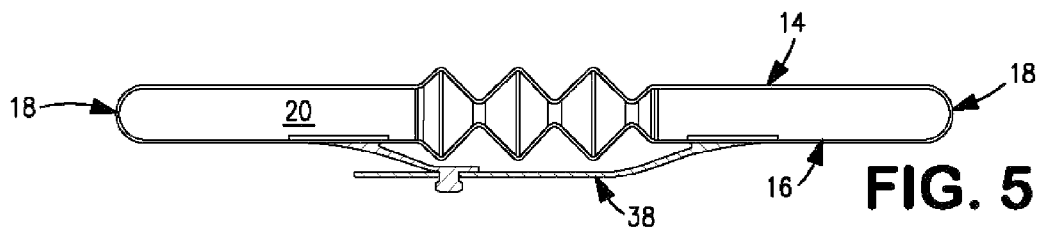
FIG. 5
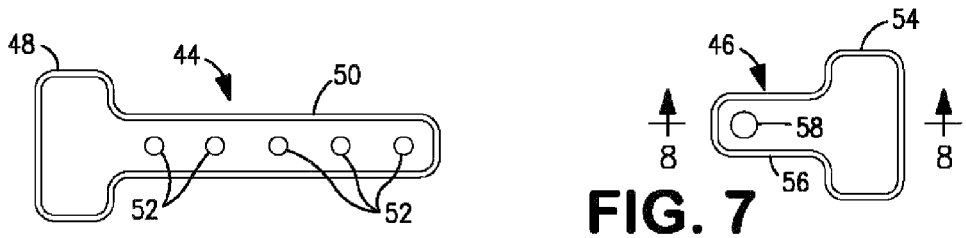
FIG. 6
FIG. 7
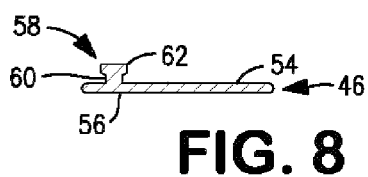
FIG. 8
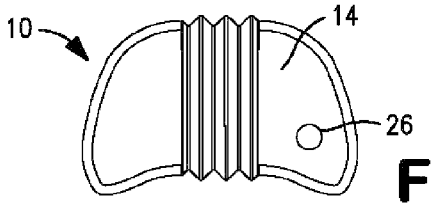
FIG. 9
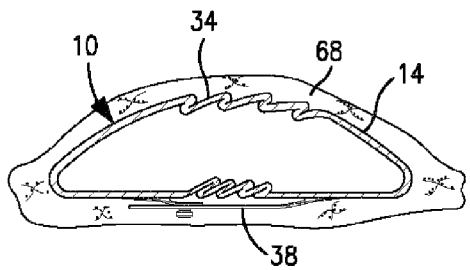
FIG. 10
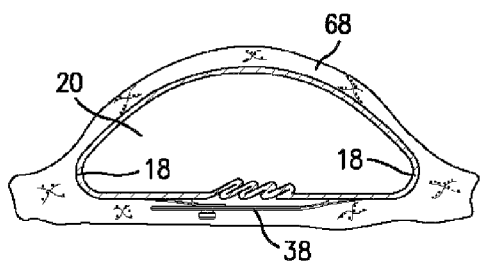
FIG. 11

DIMENSIONALLY ADJUSTABLE SOFT TISSUE EXPANDER

FIELD OF THE INVENTION

The invention relates to soft tissue expanders and to methods for expanding soft tissue and overlying skin using soft tissue expanders.

DESCRIPTION OF THE PRIOR ART

A conventional soft tissue expander may include a cover and a base joined at a boundary to define a fluid tight chamber within the expander. Among several alternatives, the base may be separate and bonded to the cover, it may consist of a bonded reinforcement, or it may simply be the deeper wall of an expander made with a continuous envelope, the wall lying against the deepest portion of the pocket. The base is generally flat and has a fixed shape determined during manufacture of the expander. An inlet port may be mounted in the cover or may be external to the expander and connected to the expander by a tube to inject liquid into the expander.

The expander is collapsed and inserted into a surgically formed pocket beneath a layer of skin and soft tissue to be expanded. After the pocket is closed, liquid is injected into the expander to elevate the cover of the expander above the base and expand the skin and tissue overlying the cover. The area of the expanded tissue is determined by the shape of the expander base.

An expander with a fixed base is not capable of fitting itself to the outlines of the adjacent defect to be addressed during the expansion. This means that the hospital must stock an inventory of tissue expanders with different size fixed bases in order to assure an expander having an appropriate size base is available for expansion of soft tissue of a desired size. Manufactures must make a range of expanders with different size fixed bases.

A known adjustable base expander is capable of expanding different size areas of overlying soft tissue and skin. U.S. Pat. No. 5,571,179 discloses an adjustable base expander having a crescent shape with a pair of arms at the ends of the expander and a folded tubular portion in the center of the expander between the arms. The area and shape of the base are varied by lengthening, contracting or bending the central portion. Maintaining the desired shape of the base of the expander during surgical implantation and until expansion is difficult because the arms and the tubular portions are free to move relative to each other. When this expander is inflated internal pressure may be sufficient to enlarge the base by expanding the folds in the tubular portion so that the area of overlying tissue is increased and an undesirably large area of soft tissue is expanded. A change in the shape of the base is undesirable because the area and shape of the expanded tissue are correspondingly changed.

When creating a pocket for a non-breast tissue expander the surgeon dissects a pocket appropriate for the expander. For an adjustable base expander, the surgeon may dissect the pocket and then place the expander within it suitably adjusting the dimensions of the expander to fit the pocket. In breast reconstruction, particularly in the case of expander placement immediately after mastectomy, the pocket is usually much larger than that which would be dissected for placement of the expander alone. This means that the expander base is unrestrained and internal pressure during inflation can increase the width of the base so that an undesirably large area of soft tissue is expanded.

Accordingly, there is a need for an improved soft tissue expander with an adjustable base which maintains its shape during implantation and expansion to assure the expanded of skin and soft tissue overlying the base have a desired size and shape. The expander should have an adjustable restraint built into the base of the expander which prevents the base from extending in width and becoming too broad for the optimum reconstruction.

There is also a need for an improved method for expanding the skin and soft tissue using a single expander where the size of the expander base is adjustable and then fixed so that the size of the soft tissue and skin to be expanded can be varied to meet particular patient requirements.

SUMMARY OF THE INVENTION

The invention is an improved soft tissue expander with an adjustable base which maintains its shape during implantation and expansion so that the size of the expanded overlying skin and soft tissue expanded is determined by the size and shape of the expander base selected by the surgeon before the expander is implanted. A single expander may be used to expand different size areas of skin and soft tissue by adjusting the shape of the base prior to implanting the expander under the skin and soft tissue to be expanded.

An expander according to the invention is useful in expanding skin and soft tissue overlying the breast of the patient prior to implanting a breast prosthesis. This procedure forms a shaped layer of skin and soft tissue conforming to the shape of the breast and having sufficient area to replace the skin removed from the lower pole of the breast during a mastectomy. Accurate shaping of the expanded skin and soft tissue to simulate the natural breast is critically important to the success of the procedure.

The use of an adjustable base expander according to the invention for expanding breast skin and soft tissue permits the surgeon to use one expander for patients having different sized breasts with the base of the expander adjusted before implantation to meet the requirements of the particular patient. The size of the expander base is readily adjusted and does not change during implantation and inflation of the expander and overlying skin and soft tissue. The expander is also useful in other soft tissue expansion procedures.

DESCRIPTION OF THE DRAWINGS

FIGS. 3 and 4 are side views of the expander of FIG. 1;

FIG. 5 is a sectional view taken along line 5-5 of FIG. 1;

FIGS. 6 and 7 are top views of strap components of the expander;

FIG. 8 is a sectional view taken along line 8-8 of FIG. 7;

FIG. 9 is a view similar to FIG. 1 illustrating an inlet port mounted in the cover of the expander;

FIG. 10 illustrates an implanted expander partially expanded;

FIG. 11 illustrates an implanted expander fully expanded;

DESCRIPTION OF THE PREFERRED EMBODIMENTS

Figure 1:
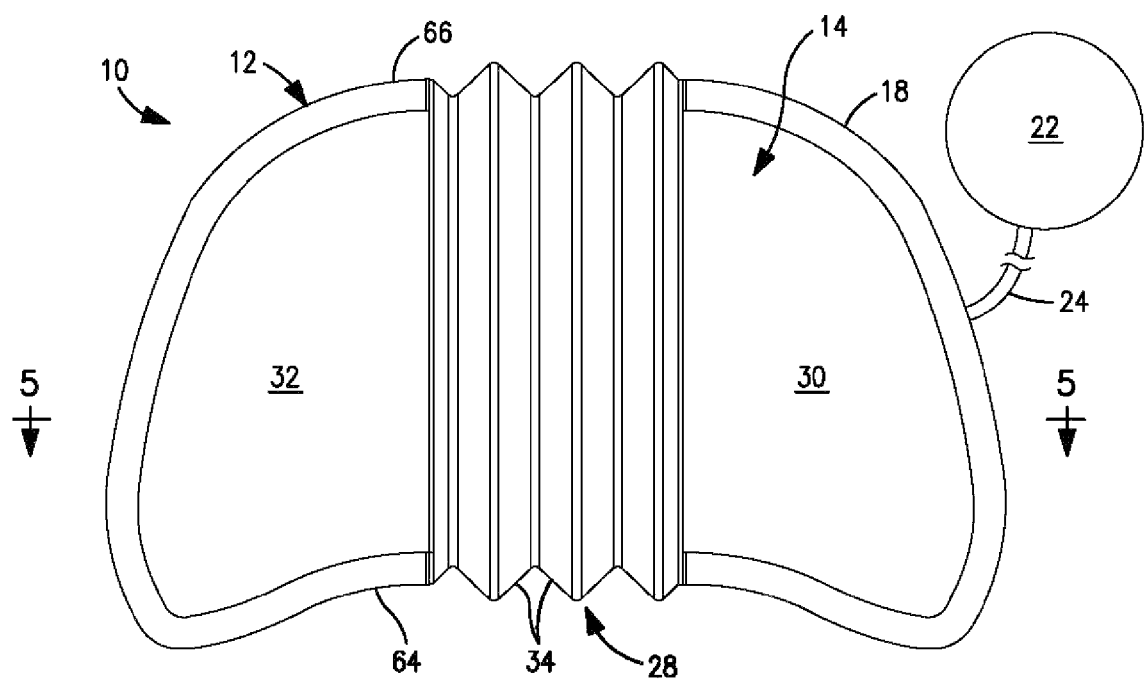
FIG. 1 is a view of the cover of a first embodiment dimensionally adjustable soft tissue expander according to the invention.

Dimensionally adjustable soft tissue expander 10 includes a generally crescent-shaped, hollow body 12 preferably integrally formed from a silicone polymer elastomer material which may be silicone rubber. The body 12 includes cover 14, base 16 located under the cover and boundary 18 extending circumferentially around the body and joining the base and cover. When the expander is collapsed, as illustrated in FIGS. 1-5, the cover and base are generally flat. The body defines a fluid tight interior chamber 20. An external inlet port 22 is connected to chamber 20 by tube 24 to permit liquid, conventionally a saline solution, to be injected into chamber 20 to inflate the expander or to be withdrawn from the chamber. Liquid is injected or withdrawn by inserting a hypodermic needle into port 22. If desired, an inlet port 26 may be mounted in cover 14 in place of external port 22, as illustrated in FIG. 9.

Expander 10 includes a tubular central portion 28 and a pair of like side portions or arms 30, 32 joined to the ends of the tubular central portion. Central portion 28 includes a number of accordion folds 34 formed in the cover, base and boundary and extending around the body. Folds 34 facilitate adjustment of the shape of the expander base 16 by moving side portions 30 and 32 toward or away from each other. Folds 34 are compliant and conform to movement of portions 30 and 32 to vary the width of the expander. Cover 14 conforms to changes in shape of base 16.

Figure 2:
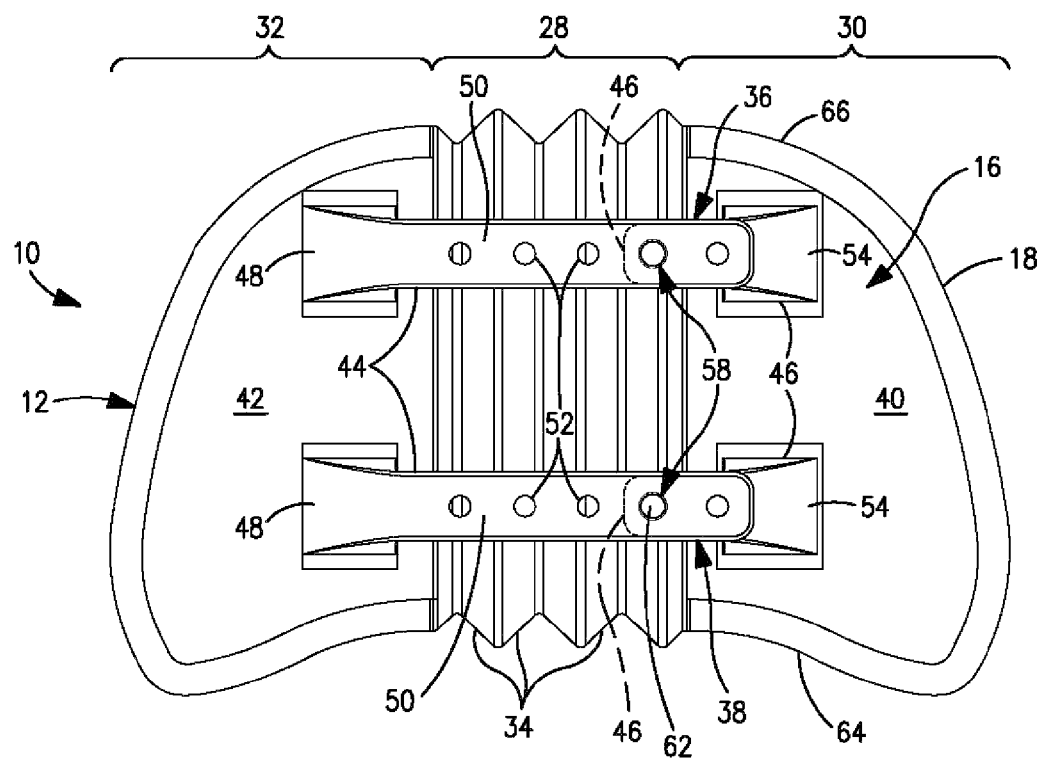
FIG. 2 is a view of the base of the expander of FIG. 1.

The expander 10 includes two like connecting members 36, 38 illustrated in FIG. 2. The members 36, 38 are integrally attached to the flat base walls 40, 42 on portions 30 and 32 and extend transversely across the folded central portion 28 on the outside of base 16. Each member 36, 38 includes two parts 44 and 46 as shown in FIGS. 6 and 7. Parts 44 and 46 are preferably formed from the same silicone polymer elastomer material forming body 12, or they may be reinforced with stiffer polymer or an embedded inelastic polymeric mesh, such as Dacron. Part 44 includes an enlarged mounting base 48 and elongate arm 50 extending outwardly from the base and having a plurality of lock openings 52 extending through the arm and spaced along the length of the arm.

Part 46 includes an enlarged mounting base 54, like base 48, and a short arm 56 extending outwardly from the base. Lock post 58 extends upwardly from the outer end of arm 56 as illustrated in FIG. 8. Post 58 includes a cylindrical portion 60 adjacent arm 56 and an enlarged head 62 on the end of portion 60. Head 62 is larger than openings 52. The cylindrical portion 60 has a tight fit in an openings 52. The mounting bases of parts 44 and 46 are connected to the outer surfaces of base portions 40 and 42 to either side of central portion 28 as shown in FIG. 2 with the arms extending toward each other over the central portion. The connections may be solvent bonds.

The adjustable parts 36, 38 are secured together by positioning of arm 50 above arm 56 with head 62 of post 58 immediately below a selected opening 52 in arm 50. One clamp member of a pliers-type tool is then placed under short arm 56 at the post and the other clamp member is placed over long arm 50 to either side of hole 52. The members are then moved together to force head 62 through the opening 52 and secure members 44 and 46 together as illustrated in FIGS. 2 and 5. Alternatively, the members may be manually secured together.

In expander 10 long arms 50 each have five lock openings 52 arranged along the length of the arm so that the width of central portion 28, and the corresponding width of the expander, may be adjusted as required. The width of expander 10 is fixed by securing members 36 and 38 together before the expander is implanted so that the shape of the base is fixed and does not change during handling, implantation, and expansion.

The expander is implanted and inflated to expand an area of overlying skin and soft tissue of desired size. When expansion of a wide area of skin and soft tissue is required, lock posts 58 are snapped into the lock opening 52 at the outer ends of long arms 50 to maximize the expander width for expansion of a maximum area of skin and soft tissue. Snapping the lock post 58 in openings 52 closer to the inner ends of arms 50 reduces the width of the expander and reduces the area of the skin and soft tissue expanded by inflation of the expander.

The expander 10 is useful in expanding skin and soft tissue overlying the breast area after a mastectomy. During the mastectomy, the breast and skin and tissue at the lower pole of the breast are surgically removed leaving a pocket under the remaining skin and soft tissue. The remaining skin and soft tissue are expanded by positioning an expander 10 in the surgically formed pocket under the skin and soft tissue and over the rib cage. An expander 10 is prepared for implantation in the pocket by adjusting the width of the expander so that it will expand an area of soft tissue and skin of appropriate size to simulate the breast. The width of the expander is adjusted by snapping the posts 58 of both connecting members in appropriate lock openings 52 as described. The width of expander central portion 28 varies depending upon the adjusted lengths of members 36 and 38.

The expander is implanted in the surgically prepared pocket with convex edge 66 at the upper pole of the pocket and concave edge 64 of the lower pole of the pocket, base 16 adjacent the rib cage and cover 14 underlying an area of soft tissue and skin to be expanded. When implanted, the flexible accordion folds 34 are flattened as indicated generally in FIG. 10. After placement of the expander in the pocket, the pocket is surgically closed and fibrous growth termed a capsule surrounds the expander and secures the expander in place.

After implantation of the expander and healing, the expander is inflated by injecting liquid into chamber 20. The ribcage supports the base of the expander and cover 14 is inflated above the base to exert pressure on and expand the overlying skin and soft tissue. FIG. 10 illustrates expander 10 partially expanded with the accordion folds 34 in cover 14 partially unfolded. FIG. 11 illustrates the expander fully expanded. Expanded tissue at lower pole replaces skin removed during the mastectomy and reestablishes the inframammary fold.

During inflation of expander 10 and expansion of overlying skin and soft tissue 68, connecting members 36 and 38 prevent separation of expander side portions 30 and 32 to assure the expander base maintains the preselected width for the procedure and the expanded tissue 68 has the desired width. If the expander did not include the members 36 and 38 the width of the expander could change during handling, implantation and expansion. The pressure exerted on the expander during injection of the liquid into chamber 20 could increase the width of the expander and undesirably increase the area of the overlying skin and soft tissue expanded by the expander. The two members 36 and 38 prevent relative rotation of side portions 30 and 32 during expansion.

After the expander 10 has been fully inflated as shown in FIG. 11 to fully expand overlying tissue 68, the liquid in the expander is withdrawn and the expander is surgically removed. A properly shaped breast prosthesis is inserted in the expander pocket and the pocket is surgically closed. The expanded soft tissue 68 has a shape simulating the natural breast with an inframammary fold at the lower pole.

The adjustable base of expander 10 permits one expander to serve all patients, regardless of the size of the overlying skin and soft tissue required for expansion. The surgeon determines the width of the expander required for the particular procedure and adjusts the width of expander 10 by adjusting the lengths of members 36 and 38 as required. As a result, one expander can may be used for all patients. Manufacturers need not make different size expanders for different size breast reconstruction. Hospital inventories of breast expanders for reconstruction are reduced because a single adjustable base expander may be used for all patients.

The mounting bases 48 and 54 on the ends of members 36 and 38 are preferably joined to side portions 30 and 32 of the expander at the base 16 by solvent bond connections 82. The members may be joined to the base by other types of connections, such as adhesive or clamp connections. Arms 44 and 46 are secured together by post-and-hole connections. Other connections may be used including buckles, clips and the like. The arms need not be flat, as illustrated, but may have different cross sections.

In expander 10 two adjustable members 36, 38 determine the width of the expander. The members prevent relative rotation of the side portions. If desired, the width of the expander may be maintained by a single member joining the side portions and extending across the central portion. A single member is preferably located midway between the top and bottom of the expander.

Expander 10 when deflated as shown in FIGS. 1 and 2, has a width greater than its height. The invention is not limited to expanders having greater width than height. A dimensionally adjustable expander according to the invention may be used for applications other than breast reconstruction. For instance, all soft tissue expanders may have adjustable bases so that one expander may serve all patients by sizing the base for a particular procedure. This reduces the number of different expanders required and eliminates the need to inventory similar expanders having different widths.

Figure 12:
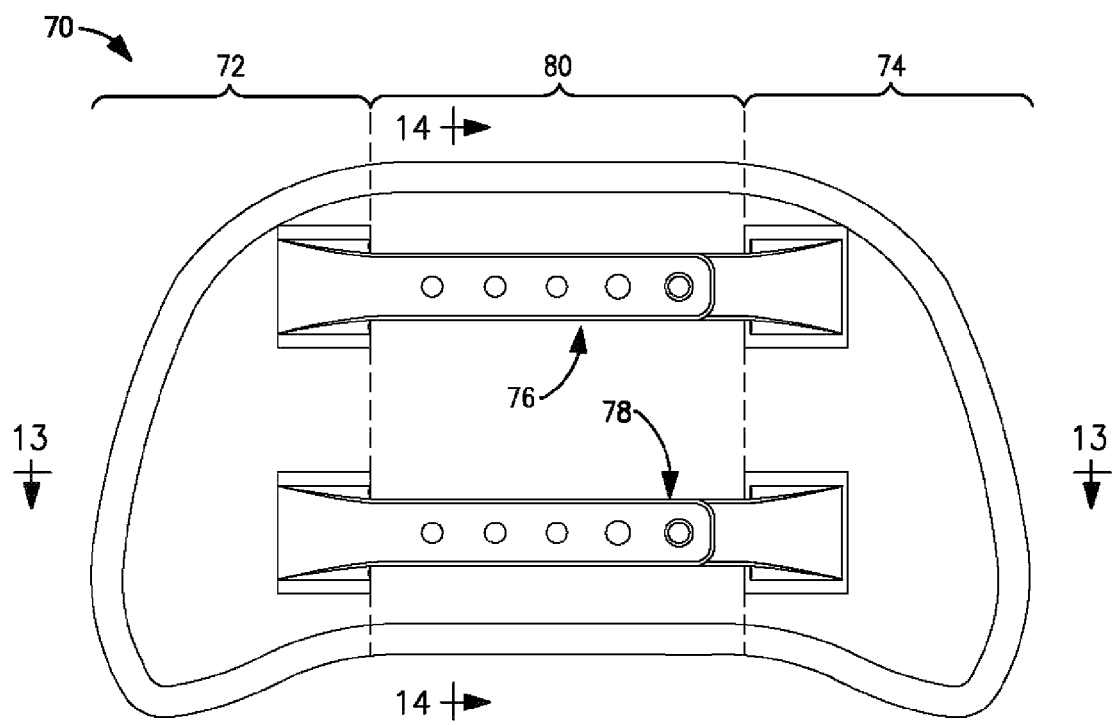
FIG. 12 is a view the base of a second embodiment dimensionally adjustable soft tissue expander according to the invention.
Figure 14:
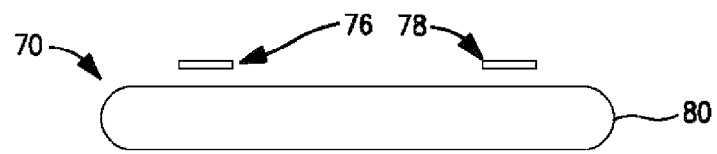
FIGS. 13 and 14 are sectional views taken along lines 13-13 and 14-14 of FIG. 12.
Figure 13:
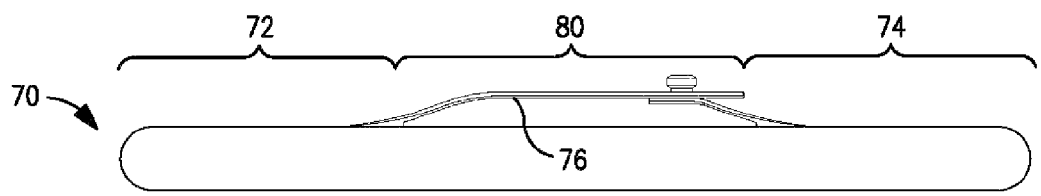

Tubular central portion 28 need not have accordion folds. FIG. 12 illustrates a second preferred embodiment dimensionally adjustable soft tissue expander 70 identical to expander 10 with side portions 72 and 74 like portions 30 and 32 and connecting members 76 and 78 like members 36 and 38. The members are shown in full width positions, with posts engaging the last, outermost lock openings. Central portion 80 is formed from a thin cylindrical portion of the body without accordion folds.

When the width of expander 70 is reduced by snapping the lock posts in openings closer to side portion 72, the width of the central portion is reduced and the central portion is folded sufficiently to accommodate the reduction. A single fold may be formed in the central portion. The expander 70 is used to expand overlying soft tissue as previously described. During handling, insertion and expansion, connecting members 76 and 78 maintain a fixed base and prevent relative rotation of the end portions.

The expanders 10 and 70 are supported by underlying bone structure and do not require reinforcement. If desired, expanders according to the invention may be used in applications where the base is not supported. For these applications, the base may have conventional reinforcement.

While I have illustrated and described preferred embodiments of our invention, it is understood that this is capable of modification, and I therefore do not wish to be limited to the precise details set forth, but desire to avail myself of such changes and alterations as fall within the purview of the following claims.

The invention claimed is:

1. An implantable soft tissue expander including a base and a cover overlying the base, the cover and base joined together at the circumference of the expander to form a fluid tight interior chamber, said base formed from a flexible material, said cover formed from a flexible elastomer material so that the cover expands above the base when liquid is flowed into the interior chamber; the cover and base defining two spaced apart side portions and a width adjustable central portion between the side portions, each side portion extending around the expander; a flat, flexible first connecting member having an adjustable fixed length, the connecting member located below the base and extending across the width of the adjustable central portion, the first connecting member having a first mounting element under the base at one side portion, a second mounting element under the base at the other side portion, a flat, flexible center portion under the base and extending between the first and second mounting elements and means for selectively adjusting the length of the center portion to one of a number of predetermined lengths; and two connections, each connection joining one mounting element to the base at the adjacent side portion; wherein during expansion of the cover and overlying soft tissue the base and the first connecting member are supported by underlying bone and the width of the expander is determined by the selectively adjusted fixed length of the center portion.

2. The expander as in claim 1 wherein the central portion includes a plurality of folds extending around the body.

3. The expander as in claim 1 including a second connecting member extending across the central portion and joined to the side portions.

4. The expander as in claim 3 wherein each connecting member includes a first arm connected to one side portion, a second arm connected to the other side portion and a lock member securing the arms together.

5. The expander as in claim 4 wherein in each connecting member one arm includes a plurality of features spaced along length of the arm and the lock member engages one of said features.

6. The expander as in claim 5 wherein said features each comprise an opening in said arm, and said lock member comprises a post on the other arm extended into an opening.

7. The expander in claim 6 wherein said post includes an enlarged head.

8. The expander as in claim 1 wherein said base and connecting member are formed from an elastomer material.

9. The expander as in claim 8 wherein said connections are solvent bonds.

10. The expander as in claim 1 wherein said body has a generally crescent shape.

11. The expander as in claim 1 wherein said central portion is generally tubular.

12. The expander as in claim 1 including an external inlet port and a tube extending from the inlet port to the interior of the body.

13. The expander as in claim 1 including an inlet port in said cover.

14. The expander as in claim 1 wherein the connecting member includes reinforcing material.

15. The expander as in claim 1 wherein the body and connection member are formed from silicone elastomer material and said connections are solvent bonds.

16. A soft tissue expander comprising:
a) a hollow body defining a fluid tight interior chamber; said body including a pressure expandable cover formed from a flexible elastomer, a flexible base under the cover, the base and cover joined together at the circumference of the body to form a fluid tight interior chamber, the body including two opposed and spaced apart side portions and a central portion between the side portions, each portion extending around the body; and
b) a first flat, flexible connecting member below the base and extending across the central portion, the connecting member having opposed ends each bonded to the base at one side portion, the connecting member underlying the central portion, the connecting member including means for selectively adjusting the length of the connecting member to one of a number of different fixed lengths, wherein the selectively adjusted length of the connecting member determines the width of the expander during pressure expansion of the cover in response to liquid flowed into the chamber.

17. The expander as in claim 16 wherein the central portion includes a fold extending around the body.

18. The expander as in claim 16 wherein the central portion is tubular.

19. The expander as in claim 16 including a second connecting member extending across the central portion and connected to the side portions at the base.

20. The expander as in claim 16 wherein the said body and connecting member are formed from a silicone elastomer and said connections are solvent bonds.

21. The expander as in claim 16 wherein the connecting member is not connected to the central the portion.

22. The expander as in claim 16 wherein said connecting member includes reinforcing material.

23. The expander as in claim 16 including a plurality of holes in the connecting member.

24. The expander as in claim 16 including a second connecting member joined to the side portions and extending freely across the central portion.

25. The expander as in claim 24 wherein each connecting member includes reinforcing material.

26. The expander as in claim 16 wherein the central portion includes a fold.

27. The expander as in claim 16 wherein the central portion is tubular.

28. The expander as in claim 16 wherein said base is crescent-shaped.

29. The expander as in claim 16 wherein said body is made of silicone rubber.

30. An implantable soft tissue expander including a base and a cover overlying the base, the cover and base joined together at the circumference of the expander to form a fluid tight interior chamber, said base formed from a flexible material, said cover formed from a flexible elastomer material so that the cover expands above the base when liquid is flowed into the interior chamber; the cover and base defining two spaced apart side portions and a width adjustable central portion between the side portions, each side portion extending around the expander; a flexible connecting member located below the base and extending across the width of the adjustable central portion, the connecting member having ends joined respectively to the side portions of the expander and a fixed length center portion between the ends and below the adjustable width central portion of the expander, wherein the width of the expander is determined by the fixed length of the center portion of the connecting member.

31. The soft tissue expander as in claim 30 wherein the fixed length of the connecting member is adjustable.

* * * * *